United States Patent
Poullain

(10) Patent No.: US 11,672,926 B2
(45) Date of Patent: Jun. 13, 2023

(54) DEVICE FOR DISPENSING A FLUID PRODUCT

(71) Applicant: APTAR FRANCE SAS, Le Neubourg (FR)

(72) Inventor: Franck Poullain, La Haye Malherbe (FR)

(73) Assignee: APTAR FRANCE SAS, Le Neubourg (FR)

( * ) Notice: Subject to any disclaimer, the term of this patent is extended or adjusted under 35 U.S.C. 154(b) by 398 days.

(21) Appl. No.: 16/755,400

(22) PCT Filed: Oct. 9, 2018

(86) PCT No.: PCT/FR2018/052492
§ 371 (c)(1),
(2) Date: Apr. 10, 2020

(87) PCT Pub. No.: WO2019/073165
PCT Pub. Date: Apr. 18, 2019

(65) Prior Publication Data
US 2020/0289769 A1   Sep. 17, 2020

(30) Foreign Application Priority Data

Oct. 12, 2017 (FR) ...................................... 1759549

(51) Int. Cl.
*A61M 15/00* (2006.01)
*A61M 11/00* (2006.01)

(52) U.S. Cl.
CPC ...... *A61M 15/0041* (2014.02); *A61M 11/007* (2014.02); *A61M 15/0036* (2014.02);
(Continued)

(58) Field of Classification Search
CPC .. A61M 11/00; A61M 11/006; A61M 11/007; A61M 11/008; A61M 11/02;
(Continued)

(56) References Cited

U.S. PATENT DOCUMENTS

| 3,906,950 A | * | 9/1975 | Cocozza | ........... A61M 15/0028 |
| | | | | 128/203.15 |
| 4,534,343 A | | 8/1985 | Nowacki et al. | |

(Continued)

FOREIGN PATENT DOCUMENTS

| GB | 1 436 028 A | 5/1976 |
| WO | 99/46055 A1 | 9/1999 |

(Continued)

OTHER PUBLICATIONS

International Preliminary Report on Patentability dated Apr. 16, 2020, in International Application No. PCT/FR2018/052492.

(Continued)

*Primary Examiner* — Colin W Stuart
(74) *Attorney, Agent, or Firm* — Sughrue Mion, PLLC

(57) ABSTRACT

A fluid dispenser device having a dispenser head; an air expeller; and a reservoir containing a single dose of fluid. The reservoir includes a proximal axial end and a distal axial end, and is removably mounted so that after the device has been actuated, the empty reservoir can be removed from the device and replaced by a new full reservoir. The air expeller is adapted to return to its rest position to enable a new actuation with the new full reservoir. The dispenser head includes a proximal perforator tip to perforate the proximal axial end of the reservoir. The device includes a movable perforator member that slides axially around the dispenser head between a loading position and an actuation position and includes a distal perforator tip adapted to perforate the (Continued)

distal axial end of the reservoir when the movable perforator member is moved into its actuation position.

17 Claims, 4 Drawing Sheets

(52) U.S. Cl.
CPC . *A61M 2202/064* (2013.01); *A61M 2205/073* (2013.01); *A61M 2205/3337* (2013.01)

(58) Field of Classification Search
CPC .. A61M 11/06; A61M 15/00; A61M 15/0001; A61M 15/0013; A61M 15/0015; A61M 15/0028; A61M 15/003; A61M 15/0033; A61M 15/0035; A61M 15/0036; A61M 15/0041; A61M 15/0061; A61M 16/206; A61M 16/20; A61M 16/208; A61M 2202/064; A61M 2205/07; A61M 2205/071; A61M 2205/073
See application file for complete search history.

(56) References Cited

U.S. PATENT DOCUMENTS

| | | | | |
|---|---|---|---|---|
| 5,619,985 | A * | 4/1997 | Ohki | A61M 15/0033 128/203.15 |
| 5,921,236 | A * | 7/1999 | Ohki | A61M 15/0033 128/203.15 |
| 6,186,141 | B1 * | 2/2001 | Pike | A61B 18/12 128/203.12 |
| 6,367,473 | B1 * | 4/2002 | Kafer | B05B 11/064 128/203.19 |
| 8,869,794 | B1 * | 10/2014 | Tuckwell | A61M 15/003 221/25 |
| 2005/0258273 | A1 * | 11/2005 | Bruna | A61M 15/08 239/333 |
| 2007/0060868 | A1 | 3/2007 | Tsutsui | |
| 2010/0108062 | A1 * | 5/2010 | Ganem | A61M 15/0028 128/203.21 |
| 2010/0175696 | A1 * | 7/2010 | Ishizeki | A61M 15/08 128/203.15 |
| 2015/0059747 | A1 * | 3/2015 | Von Schuckmann | A61M 15/0035 128/203.15 |
| 2019/0116879 | A1 * | 4/2019 | Zuber | A61M 11/02 |
| 2019/0201640 | A1 * | 7/2019 | Von Schuckmann | A61M 15/0028 |

FOREIGN PATENT DOCUMENTS

| | | |
|---|---|---|
| WO | 02/45866 A1 | 6/2002 |
| WO | 2015/001269 A1 | 1/2015 |

OTHER PUBLICATIONS

International Search Report for PCT/FR2018/052492, dated Feb. 11, 2019.

* cited by examiner

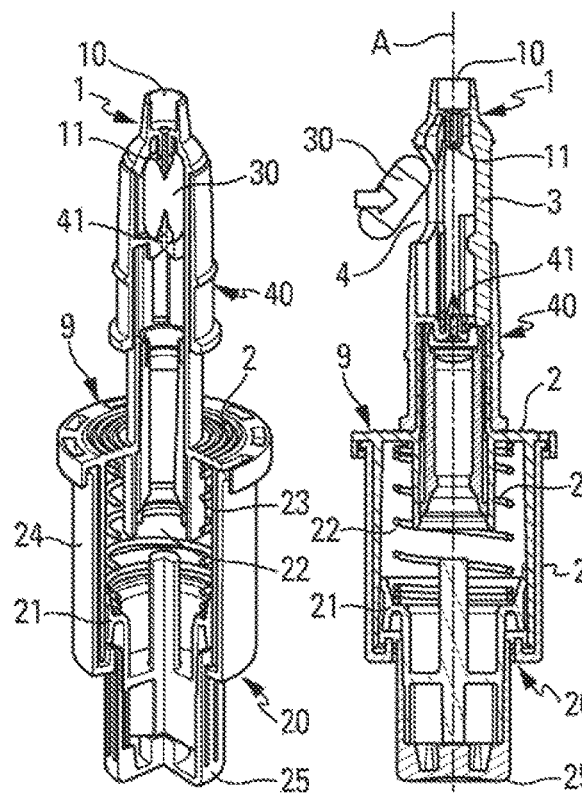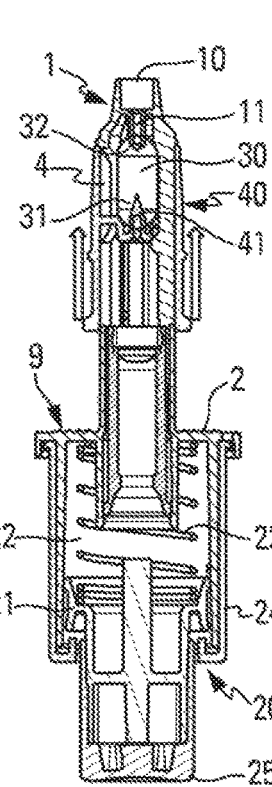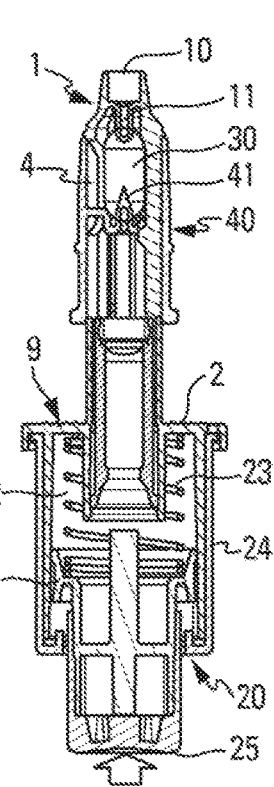
Fig. 1　　Fig. 2　　Fig. 3　　Fig. 4
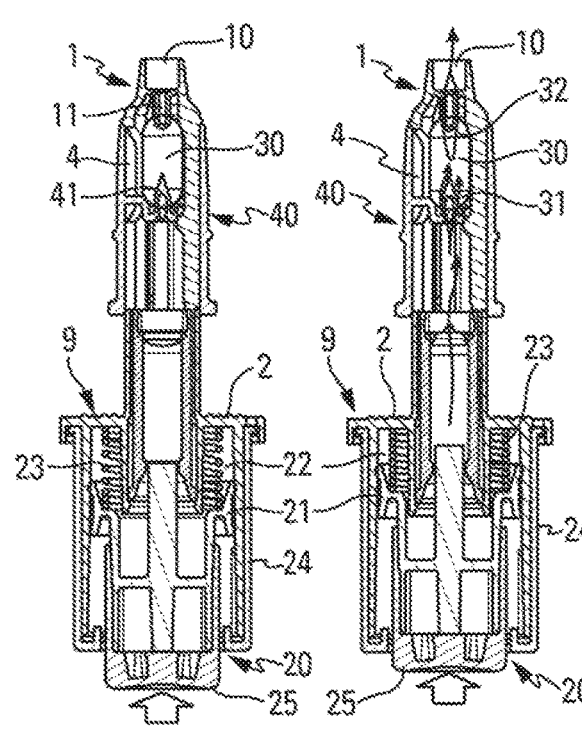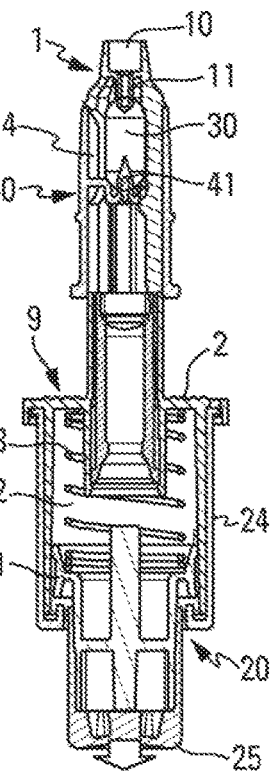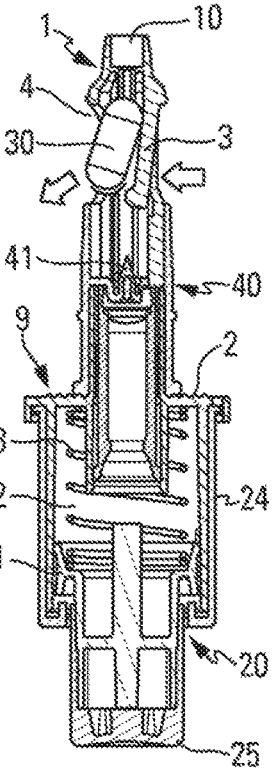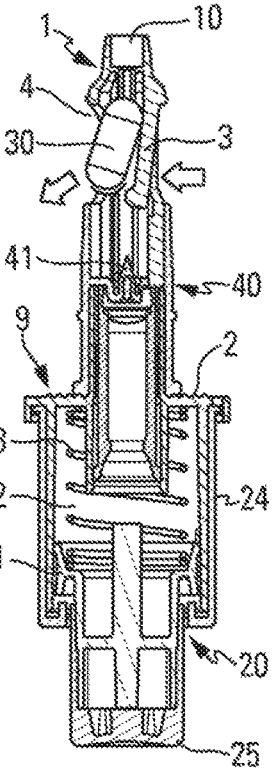
Fig. 5　　Fig. 6　　Fig. 7　　Fig. 8

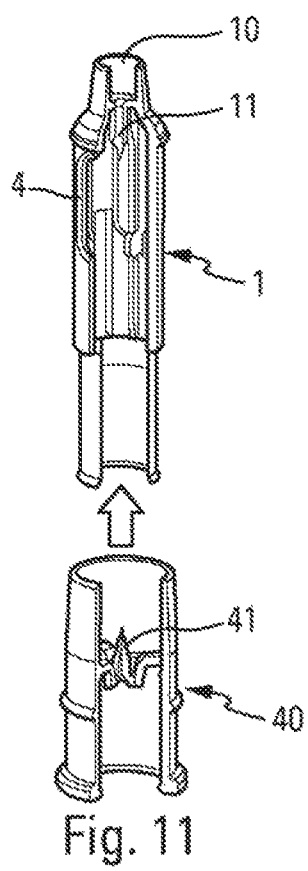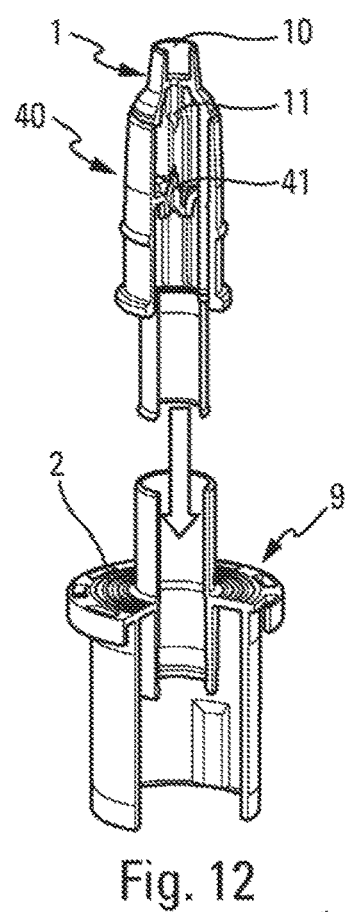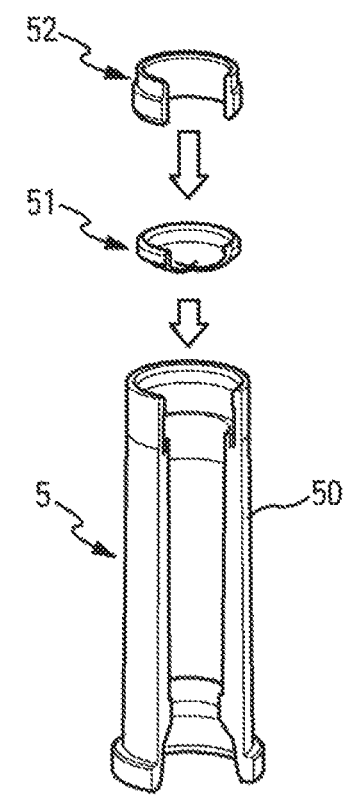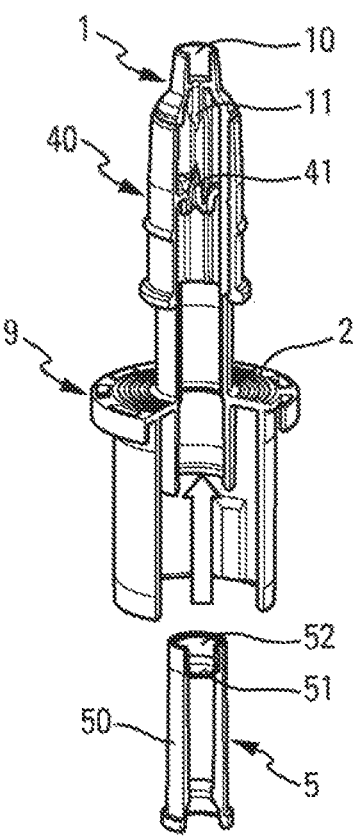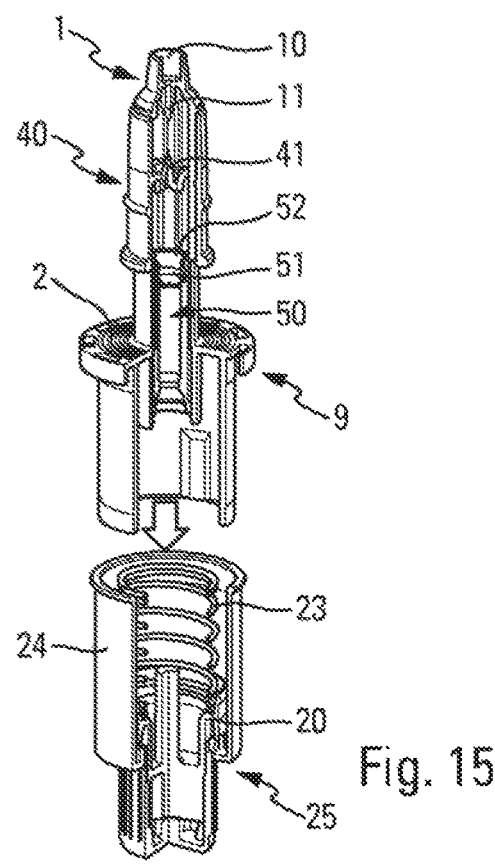
Fig. 11
Fig. 12
Fig. 13
Fig. 14
Fig. 15

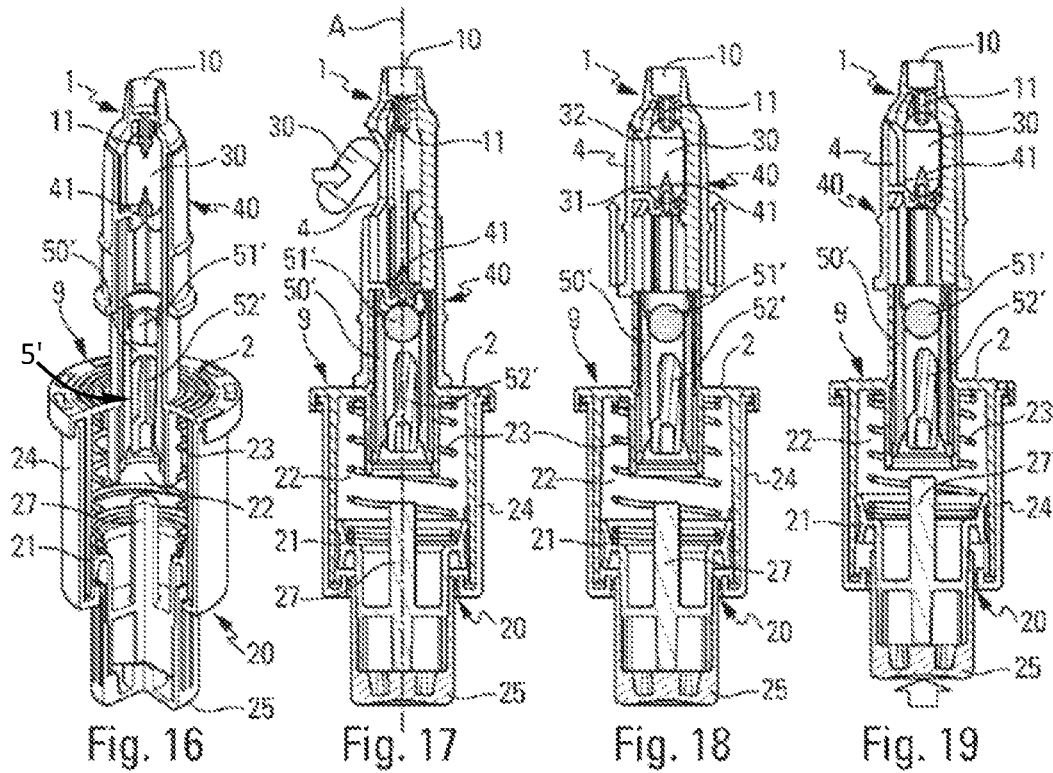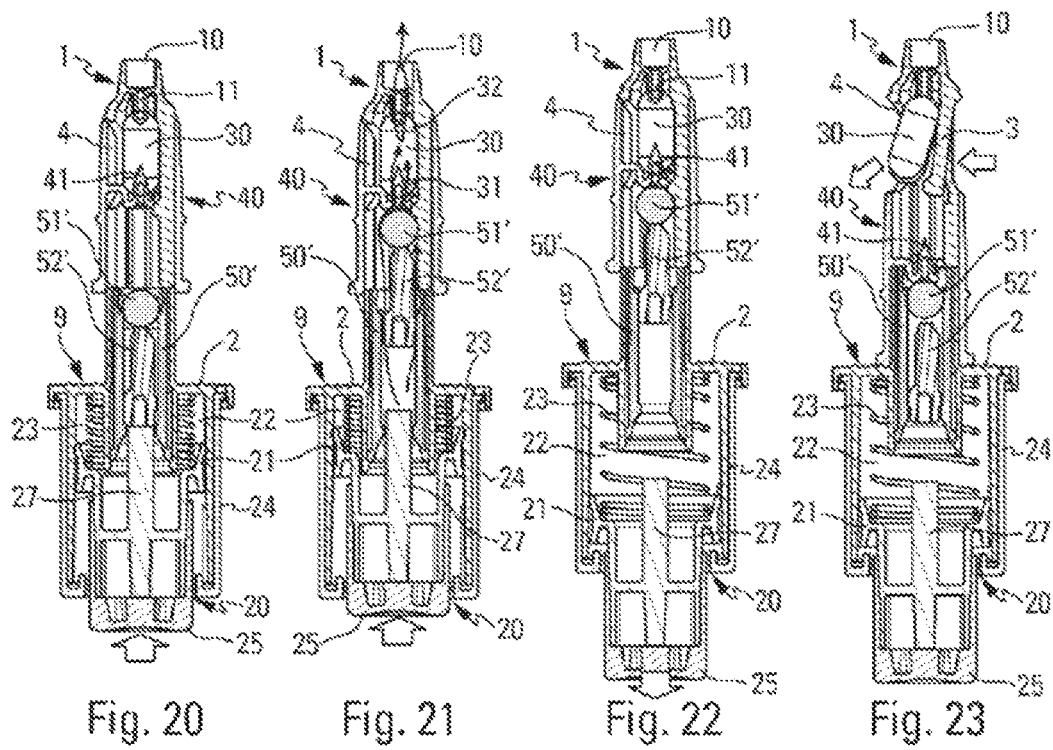

DEVICE FOR DISPENSING A FLUID PRODUCT

CROSS REFERENCE TO RELATED APPLICATIONS

This application is a National Stage of International Application No. PCT/FR2018/052492 filed Oct. 9, 2018, claiming priority based on French Patent Application No. 1759549 filed Oct. 12, 2017.

The present invention relates to a dispenser device for dispensing a fluid, and more particularly it relates to a device for dispensing a dose of fluid, in particular of powder, contained in a reservoir, by means of a flow of air under pressure.

Document WO 99/46055 discloses such a device in which a spherical closure element, which closes the outlet of the reservoir, is expelled by the flow of air created by an air expeller. In order to use a dispenser device more particularly for dispensing powder, the air pressure necessary for actuating the device must be sufficiently high to guarantee that the dose is dispensed completely, and that it is broken up, if that is necessary. In the above-mentioned device, the air pressure necessary to actuate the device is determined by the resistance opposed by the ball in order to be expelled. That resistance is relatively difficult to control and to predetermine since it depends on the friction between the ball and its cylindrical seat in which it is engaged for the purpose of closing said reservoir in sealed manner. Consequently, it may be necessary to minimize the interference between the sphere and its cylindrical seat, and obviously that might spoil the effectiveness of the closure. Furthermore, it may be necessary to minimize the depth and the positioning of the sphere in its seat so as to make it easier to expel. It may also be necessary to provide air pressure that is relatively high, which is not always easy to achieve by means of a pump system or of a bellows system, in particular when the air expellers are actuated manually by the patient. Furthermore, dispensing, i.e. expelling the ball from its seat, may take place at different positions along the stroke of the pump or of the bellows of the air expeller, such that the precise moment of dispensing the composition cannot always be predetermined in exact manner. Finally, there is a limit on the materials that can be chosen for the sphere and for its seat.

Document WO 02/45866 describes a device in which a closure ball is expelled mechanically by a rod that is secured to an air expeller. That device is not reusable, and the entire device must be thrown away after it has been used. In particular, for ecological and economic reasons, it may be desirable to have a reusable device in which the reservoir is changed after each actuation, but not the air expeller.

Document WO 2015/001269 describes a device similar to the device in document WO 02/45866, in which the air expeller of the device can be reused with a plurality of powder reservoirs. That device also presents drawbacks. Thus, it enables the air expeller to be reused, but not the dispenser head which is thrown away with the reservoir after each use. Furthermore, that device requires a movable part that is connected to the reservoir via breakable bridges, which makes the device difficult to manufacture. Furthermore, during actuation, a sound is generated when the breakable bridges are broken, which can mislead the user. In addition, the devices in documents WO 2015/001269 and WO 02/45866 include a rod that passes through the reservoir, thereby limiting the working volume of said reservoir, and making the reservoir more difficult to fill.

Document GB 1 436 028 describes a dispenser device for dispensing a capsule, in which device the capsule is inserted via the top then perforated while screw-fastening the end-piece, the perforator tip being formed on a movable member that serves solely to expel the empty capsule axially.

Documents US 2007/060868, U.S. Pat. No. 4,534,343, and US 2005/258273 describe other prior-art devices.

An object of the present invention is to provide a fluid dispenser device that does not have the above-mentioned drawbacks.

In particular, an object of the present invention is to provide such a fluid dispenser device that can be re-used a plurality of times with a plurality of different reservoirs.

An object of the present invention is also to provide a fluid dispenser device that is simple and inexpensive to manufacture, to assemble, to fill, and to use.

The present invention thus provides a fluid dispenser device comprising: a dispenser head provided with a dispenser orifice; an air expeller for generating a flow of air while the device is being actuated; and a reservoir containing a single dose of fluid, said reservoir including a proximal axial end and a distal axial end, and being mounted in removable manner in said dispenser head so that after the device has been actuated, the empty reservoir can be removed from said device and replaced by a new full reservoir, said air expeller being adapted to return to its rest position so as to enable a new actuation with said new full reservoir, said dispenser head including a proximal perforator tip that is adapted to perforate said proximal axial end of said reservoir, and said device including a movable perforator member that is arranged to slide axially around said dispenser head between a loading position and an actuation position, said movable perforator member including a distal perforator tip that is adapted to perforate the distal axial end of said reservoir when said movable perforator member is moved into its actuation position.

Advantageously, said reservoir is symmetrical.

Advantageously, said reservoir is a capsule.

Advantageously, said proximal and distal perforator tips are hollow, and each includes at least one axial opening.

Advantageously, said distal perforator tip forms an air inlet in said reservoir, said air inlet being connected to said air expeller, and said proximal perforator tip forms a fluid outlet in said reservoir, said fluid outlet being connected to said dispenser orifice, such that while the device is being actuated, the flow of air generated by the air expeller penetrates into said reservoir through said air inlet, and drives said fluid out from said reservoir through said fluid outlet, towards said dispenser orifice.

Advantageously, said proximal axial end of said reservoir is perforated by said proximal perforator tip while said reservoir is being inserted into said dispenser head.

Advantageously, said dispenser head includes a side window, arranged in the proximity of said proximal perforator tip, so as to enable said reservoir to be inserted into said dispenser head.

Advantageously, said dispenser head includes a movable or deformable portion, such as a spring blade, remote from said side window, so as to expel the empty reservoir out from said dispenser head, through said side window.

Advantageously, said air expeller includes a piston that slides in an air chamber between a rest position and a dispensing position, said air expeller including an outlet member that enables the air in said air chamber to be compressed during actuation, a return spring being provided so as to urge said piston resiliently towards its the rest position.

Advantageously, said piston, when in its rest position, co-operates in non-airtight manner with said air chamber, in such a manner that said air chamber is in communication with the atmosphere in the rest position.

In a first advantageous variant, said outlet member of the air expeller comprises a valve that passes from a closed position to an open position once the air pressure in said air chamber has reached a predetermined threshold.

Advantageously, said valve comprises a slotted diaphragm that is closed in airtight manner in the closed position, and that deforms so as to open said slot once a predetermined pressure threshold has been reached.

Advantageously, in its closed position, said diaphragm is convex towards said air chamber, and when the pressure threshold is reached, it inverts its shape and becomes concave, thereby making it possible for the slot to open.

In a second advantageous variant, said outlet member of the air expeller comprises a ball that is moved from a closed position to an open position once said piston has reached a predetermined actuation stroke in said air chamber.

Advantageously, after said piston has passed through a predetermined fraction of the actuation stroke, a central rod secured to said piston co-operates with said ball so as to expel it mechanically from its closed position.

Advantageously, said movable perforator member, when it is returned from its actuated position to its loading position, co-operates with said ball so as to return it to its closed position.

These and other characteristics and advantages appear more clearly from the following detailed description, given by way of non-limiting example, and with reference to the accompanying drawings, in which:

FIG. 1 is a diagrammatic and partially cut-away perspective view of a fluid or powder dispenser device, in a first advantageous embodiment, in its rest position;

FIG. 2 is a diagrammatic section view of the FIG. 1 device, during insertion of a capsule;

FIGS. 3 to 8 are views similar to the view in FIG. 2, showing various stages of actuation;

FIGS. 11 to 15 are diagrammatic and partially cut-away perspective views of the various stages of assembling the FIG. 1 device;

FIG. 16 is a view similar to the view in FIG. 1, showing a second advantageous embodiment; and FIGS. 17 to 23 are views similar to the views in FIGS. 2 to 8 of the FIG. 16 device.

Figure 9:
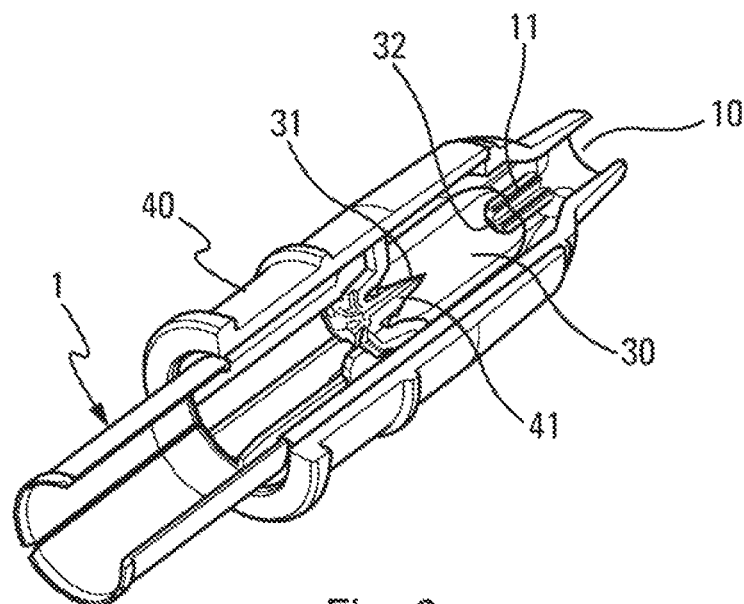
FIG. 9 is a diagrammatic and partially cut-away perspective view of a detail of the perforator means of the FIG. 1 device.

In the description below, it should be understood that the terms "upper", "lower", "upwards", and "downwards" are relative to the upright position of the device shown in particular in FIGS. 1 to 8 and 11 to 23. The terms "axial" and "radial" are relative to the longitudinal central axis A of the device shown in FIGS. 2 and 17. The terms "proximal" and "distal" are relative to the dispenser orifice.

The device includes a reservoir 30 containing a dose of fluid to be dispensed, in particular medication in the form of powder. Said reservoir 30 is preferably made in the form of a sealed capsule (which could be a gel capsule) of shape that is axially elongate. In use, the reservoir 30 is intended to be perforated at both of its axial ends, so as to form firstly an air inlet 31 at its distal axial end, and secondly a fluid outlet 32 at its proximal axial end. The air inlet 31 is connected to an air expeller 20, and the fluid outlet 32 is connected to a dispenser orifice 10 of the device. Before the device is actuated, the dose of fluid to be dispensed is thus held in leaktight manner in said capsule 30.

Advantageously, and as can be seen in FIGS. 1 to 9 and 16 to 23, the reservoir 30 is symmetrical, such that the reservoir may be used in either of its axial orientations.

The device includes an air expeller 20 that is actuated manually by the user, and that is adapted to create a flow of air that passes through the reservoir 30 so as to deliver the fluid that it contains towards the dispenser outlet 10.

The reservoir 30 is inserted, in particular fitted, in a dispenser head 1 that includes the dispenser orifice 10.

Said dispenser head 1 includes a proximal perforator tip 11 that is adapted to perforate the proximal axial end of the reservoir 30 so as to form the fluid outlet 32. As can be seen in particular in FIG. 10a, the proximal perforator tip 11 is hollow and includes at least one and preferably a plurality of axial openings 111 that are preferably arranged around the periphery of said tip. Thus, when said proximal perforator tip 11 penetrates into the reservoir 30, the fluid contained in said reservoir 30 can pass through said axial openings 111, so as to be expelled through the dispenser orifice 10.

Said dispenser head 1 includes a side window 4, arranged in the proximity of said proximal perforator tip 11, so as to enable the reservoir 30 to be inserted into said dispenser head, as shown in FIGS. 2 and 17. Advantageously, such insertion causes the proximal axial end of the reservoir 30 to be perforated by said proximal perforator tip 11.

Figure 10A:
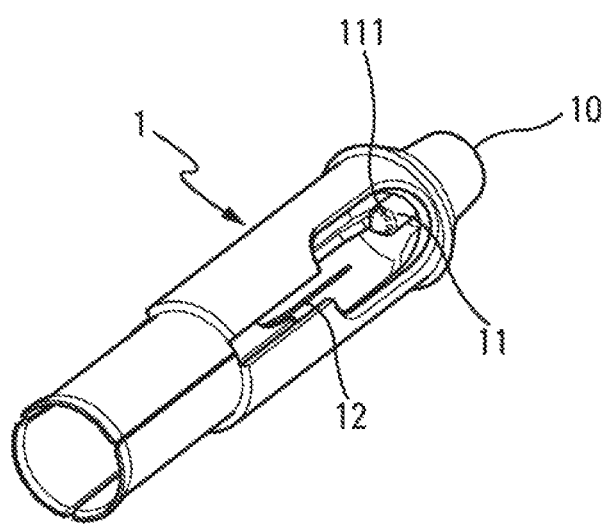
FIGS. 10a and 10b are diagrammatic perspective views respectively of the dispenser head and of the movable perforator member in FIG. 9.

Said dispenser head 1 includes a plurality of longitudinal slots 12, in particular three longitudinal slots, that can be seen in particular in FIG. 10a and having a function that is described below.

The dispenser head 1 is preferably made as single piece, in particular by molding.

A movable perforator member 40 is arranged to slide axially around said dispenser head 1 between a loading position and an actuated position. The movable perforator member 40 includes a distal perforator tip 41 that is adapted to perforate the distal axial end of the reservoir 30 so as to form the air inlet 31. As can be seen in particular in FIG. 10b, the distal perforator tip 41 is also hollow and includes at least one and preferably a plurality of axial openings 411 that are preferably arranged around the periphery of said tip. Thus, when said distal perforator tip 41 penetrates into the reservoir 30, the compressed air contained in said air expeller 20 can pass through said axial openings 411, so as to drive the fluid contained in the reservoir 30 towards said dispenser orifice 10.

Figure 10B:
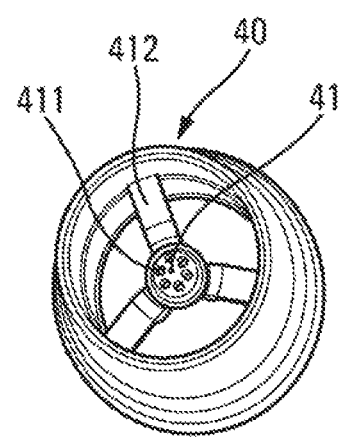

The distal perforator tip 41 is arranged centrally inside the movable perforator member 40, being fastened to the body of said movable perforator member 40 via a plurality of spacers 412, in particular three spacers, that can be seen in particular in FIG. 10b. The spacers 412 are adapted to slide axially in the corresponding longitudinal slots 12 of the dispenser head 1.

In the loading position, said movable perforator member 40 does not close said side window 4 of said dispenser head 1, as can be seen in FIGS. 2, 8, 17, and 23. In the actuation position, as can be seen in FIGS. 1, 3 to 7, 16 and 18 to 22, said movable perforator member 40 has been slid axially upwards around the dispenser head 1, with the effect firstly of closing said side window 4, and secondly of perforating the distal axial end of the reservoir 30 with said distal perforator tip 41, as can be seen in particular in FIGS. 3 and 18. In this position, both axial ends of the reservoir 30 are thus perforated, respectively by the proximal tip 11 and the distal tip 41, and the device is ready to be actuated.

The air expeller 20 shown in the figures includes a piston 21 that slides in an air chamber 22 between a rest position and a dispensing position, the piston 21 being actuated manually by the user. Advantageously, such actuation is performed by means of a pusher element 25 that is assembled on, or secured to, said piston 21. A return spring 23 urges said piston 21, and thus also the pusher element 25, resiliently towards their rest positions.

The air chamber 22 is formed in a lower body 9 that is also provided with a finger rest 2. The finger rest includes fastener means, in particular snap-fastener means, for fastening a sleeve 24 forming an abutment for protecting the piston 21 and the pusher element 25 against being pulled out.

In the rest position, as can be seen in FIGS. 1, 2, 8, 16, 17, and 23, the air expeller 20 is advantageously open to the atmosphere.

A first embodiment is shown in FIGS. 1 to 8. In this embodiment, a valve assembly 5 (see FIG. 13) is provided so as to enable the air contained in the air chamber 22 to be compressed at the start of actuation. The valve assembly 5 comprises a central body 50 in which there is assembled a valve 51 forming the outlet member of the air expeller 20. The valve 51 advantageously comprises a slotted diaphragm that is closed in airtight manner in the closed position, and that deforms so as to open said slot once a predetermined pressure threshold has been reached. In the embodiment shown, in its closed position, the diaphragm is convex towards the air chamber 22, and when the pressure threshold is reached, it inverts its shape and becomes concave, thereby making it possible for the slot to open. The valve 51 is held in the central body 50 by an appropriate blocking element 52.

FIGS. 11 to 15 show an advantageous way of assembling the device in FIGS. 1 to 8. Thus, as can be seen in FIG. 11, the movable perforator member 40 is firstly assembled around the dispenser head 1. Then, as can be seen in FIG. 12, the sub-assembly is mounted on the lower body 9. FIG. 13 shows how the valve assembly 5 is assembled, and specifically it shows the valve 51 and its blocking element 52 being inserted into the central body 50. FIG. 14 shows how the valve assembly 5 is assembled in the unit formed by the lower body 9 and the dispenser head 1. Finally, FIG. 15 shows the final steps of assembling the air expeller 20 with the piston 21, the pusher element 25, and the return spring 23.

Actuation of the device of the first embodiment is shown by way of example in FIGS. 2 to 8.

Thus, when it is desired to actuate the device, the user firstly places fingers on the finger rest 2 of the lower body 9, and secondly a thumb on the pusher element 25, and exerts an actuation force that moves the piston 21 towards its dispensing position. At the beginning of actuation, as can be seen in FIG. 4, the piston 21 of the air expeller co-operates in airtight manner with the air chamber 22, such that the air contained in said air chamber 22 is compressed progressively during actuation.

When the opening threshold of the valve 51 is reached, said valve opens, thereby enabling the compressed air in the air chamber 22 to flow through said valve 51 and through the distal perforator tip 41 to the reservoir 30, so as to drive the fluid contained in the reservoir towards the dispenser orifice 10.

A complete actuation stroke thus expels the entire dose of fluid contained in the reservoir 30 by means of the flow of compressed air created by the air expeller 20, as can be seen in FIG. 6.

When the user relaxes pressure on the pusher element 25, the return spring returns the piston 21 and the pusher element 25 into their rest positions. During the return stroke, air can be sucked into the air chamber 22 through the valve 51.

FIGS. 16 to 23 show a second advantageous embodiment. It is very similar to the above-described first embodiment, and differs only in the outlet member of the air expeller 20.

In the second embodiment, the valve 51 is replaced by a ball 51'. The ball 51' forms part of a ball assembly 5' comprising a central body 50' in which said ball 51' is force fitted. A thrust member 52', preferably a hollow thrust member, may be mounted to slide in said central body 50'.

The device in the second embodiment is assembled in very similar manner to the device described with reference to FIGS. 11 to 15, with the difference that the valve assembly 5 of the first embodiment is replaced by the ball assembly 5' in this embodiment.

Actuation of the device of the second embodiment is shown by way of example in FIGS. 17 to 23, and is very similar to actuation of the device of the first embodiment described above with reference to FIGS. 2 to 8.

The difference relates to opening the outlet member of the air expeller 20, formed by the ball 51' in this embodiment. As can be seen in FIG. 20, after said piston 21 has passed through a fraction of the actuation stroke, and the air contained in the air chamber 22 has thus been compressed, a central stem 27 secured to the piston 21 and/or to the pusher element 25 starts to co-operate with the thrust member 52'. Continued actuation thus moves said thrust member 52' axially upwards in said central body 50', so as to expel the ball 51' mechanically out from said central body 50', as can be seen in FIG. 21. Thus, in this variant, it is not the pressure of the compressed air in the air chamber 22 that opens the outlet member of the air expeller 20, but rather the outlet member is opened mechanically once the piston 21 has passed through a predetermined actuation stroke. The compressed air can then penetrate into the reservoir 30 so as to expel its contents. When the movable perforator member 40 is returned to its loading position, it returns the ball 51' and the thrust member 52' to their start positions inside the central body 50', as can be seen in FIG. 23. It should be observed that the thrust member 52' is not essential, and that the central rod 27 could co-operate directly with the ball 51' so as to expel it.

In all of its variants, the present invention relates to a refillable device.

Thus, after actuation, the user can remove the empty reservoir 30. Advantageously, such removal may be performed by means of a movable or deformable portion 3 of the dispenser head 1, such as a spring blade, remote from said side window 4. As can be seen in FIGS. 8 and 23, pressing sideways on said movable or deformable portion 3 pushes the empty reservoir out from the dispenser head 1, through said side window 4. After the empty reservoir has been removed, a new full reservoir 30 can be inserted into the dispenser head 1 for the next actuation.

Thus, an advantage of the present invention is that the entire device is reusable. Only the reservoir 30 is replaced and thrown away after each actuation.

The present invention is described above with reference to several embodiments, but naturally any modification could be applied thereto by a person skilled in the art, without going beyond the ambit of the present invention, as defined by the accompanying claims.

The invention claimed is:

1. A fluid dispenser device comprising: a dispenser head provided with a dispenser orifice; an air expeller for generating a flow of air while the device is being actuated; and a reservoir containing a single dose of fluid, said reservoir including a proximal axial end and a distal axial end, and being mounted in removable manner in said dispenser head so that after the device has been actuated, the empty reservoir can be removed from said device and replaced by a new full reservoir, said air expeller being adapted to return to its rest position so as to enable a new actuation with said new full reservoir, said device being characterized in that said dispenser head includes a proximal perforator tip that is adapted to perforate said proximal axial end of said reservoir, and in that it includes a movable perforator member that is arranged to slide axially around said dispenser head between a loading position and an actuation position, said movable perforator member including a distal perforator tip that is adapted to perforate the distal axial end of said reservoir when said movable perforator member is moved into its actuation position.

2. The device according to claim 1, wherein said reservoir is symmetrical.

3. The device according to claim 1, wherein said reservoir is a capsule.

4. The device according to claim 1, wherein said proximal and distal perforator tips are hollow, and each includes at least one axial opening.

5. The device according to claim 1, wherein said distal perforator tip forms an air inlet in said reservoir, said air inlet being connected to said air expeller, and said proximal perforator tip forms a fluid outlet in said reservoir, said fluid outlet being connected to said dispenser opening orifice, such that while the device is being actuated, the flow of air generated by the air expeller penetrates into said reservoir through said air inlet, and drives said fluid out from said reservoir through said fluid outlet, towards said dispenser orifice.

6. The device according to claim 1, wherein said proximal axial end of said reservoir is perforated by said proximal perforator tip while said reservoir is being inserted into said dispenser head.

7. The device according to claim 1, wherein said dispenser head includes a side window, arranged in the proximity of said proximal perforator tip, so as to enable said reservoir to be inserted into said dispenser head.

8. The device according to claim 7, wherein said dispenser head includes a movable or deformable portion remote from said side window, so as to expel the empty reservoir out from said dispenser head, through said side window.

9. The device according to claim 8, wherein the movable or deformable portion is a spring blade.

10. The device according to claim 1, wherein said air expeller includes a piston that slides in an air chamber between a rest position and a dispensing position, said air expeller including an outlet member that enables the air in said air chamber to be compressed during actuation, a return spring being provided so as to urge said piston resiliently towards its the rest position.

11. The device according to claim 10, wherein said piston, when in its rest position, co-operates in non-airtight manner with said air chamber, in such a manner that said air chamber is in communication with the atmosphere in the rest position.

12. The device according to claim 10, wherein said outlet member of the air expeller comprises a valve that passes from a closed position to an open position once the air pressure in said air chamber has reached a predetermined threshold.

13. The device according to claim 12, wherein said valve comprises a slotted diaphragm that is closed in airtight manner in the closed position, and that deforms so as to open said slot once a predetermined pressure threshold has been reached.

14. The device according to claim 13, wherein, in its closed position, said diaphragm is convex towards said air chamber, and when the pressure threshold is reached, it inverts its shape and becomes concave, thereby making it possible for the slot to open.

15. The device according to claim 10, wherein said outlet member of the air expeller comprises a ball that is moved from a closed position to an open position once said piston has reached a predetermined actuation stroke in said air chamber.

16. The device according to claim 15, wherein, after said piston has passed through a predetermined fraction of the actuation stroke, a central rod secured to said piston co-operates with said ball so as to expel it mechanically from its closed position.

17. The device according to claim 16, wherein said movable perforator member, when it is returned from its actuated position to its loading position, co-operates with said ball so as to return it to its closed position.

* * * * *